US011147624B2

United States Patent
Xia et al.

(10) Patent No.: US 11,147,624 B2
(45) Date of Patent: Oct. 19, 2021

(54) PATTERN LASER

(71) Applicant: Ellex Medical Pty Ltd, Adelaide (AU)

(72) Inventors: Wei Xia, Adelaide (AU); Eric Benson, Adelaide (AU); Yong Min Ooi, Adelaide (AU); Victor Previn, Adelaide (AU); Timothy Dixon, Adelaide (AU)

(73) Assignee: ELLEX MEDICAL PTY LTD, Adelaide (AU)

( * ) Notice: Subject to any disclaimer, the term of this patent is extended or adjusted under 35 U.S.C. 154(b) by 261 days.

(21) Appl. No.: 16/062,078

(22) PCT Filed: Dec. 14, 2016

(86) PCT No.: PCT/AU2016/051228
§ 371 (c)(1),
(2) Date: Jun. 13, 2018

(87) PCT Pub. No.: WO2017/100839
PCT Pub. Date: Jun. 22, 2017

(65) Prior Publication Data
US 2018/0368915 A1      Dec. 27, 2018

(30) Foreign Application Priority Data
Dec. 14, 2015   (AU) ................................ 2015905168

(51) Int. Cl.
*A61B 18/00* (2006.01)
*A61B 18/20* (2006.01)
(Continued)

(52) U.S. Cl.
CPC ........ *A61B 18/203* (2013.01); *A61F 9/00821* (2013.01); *A61B 2018/2211* (2013.01);
(Continued)

(58) Field of Classification Search
None
See application file for complete search history.

(56) References Cited

U.S. PATENT DOCUMENTS

| 5,178,617 A | 1/1993 | Kuizenga et al. |
| 7,090,670 B2 | 8/2006 | Sink |

(Continued)

FOREIGN PATENT DOCUMENTS

| EP | 0226336 A2 | 6/1987 |
| JP | 2009-514564 A | 4/2009 |

(Continued)

OTHER PUBLICATIONS

WIPO Application No. PCT/AU2016/051228, PCT International Preliminary Report on Patentability dated Aug. 28, 2017.

(Continued)

*Primary Examiner* — Ankit D Tejani
(74) *Attorney, Agent, or Firm* — Alston & Bird LLP

(57) ABSTRACT

The invention resides in a pattern laser comprising a plurality of laser devices each emitting a treatment laser beam into an optical fibre of an optical fibre bundle. An optical coupling module is associated with each laser device and each optical fibre for coupling a treatment laser beam into the associated optical fibre. A controller controls the operation of the laser devices by selectively turning on or off one or more of the laser devices so as to form a laser treatment pattern at an end of the fibre bundle away from the laser devices. A delivery system images the output from the fibre bundle to a treatment zone.

18 Claims, 3 Drawing Sheets

(51) Int. Cl.
*A61F 9/008* (2006.01)
*A61B 18/22* (2006.01)

(52) U.S. Cl.
CPC ............... *A61F 2009/00863* (2013.01); *A61F 2009/00897* (2013.01)

(56) References Cited

U.S. PATENT DOCUMENTS

| | | | |
|---|---|---|---|
| 8,876,808 | B2 | 11/2014 | Feklistov et al. |
| 9,060,846 | B2 | 6/2015 | Feklistov et al. |
| 9,468,775 | B2 | 10/2016 | Plunkett |
| 10,369,051 | B2 | 8/2019 | Plunkett et al. |
| 2005/0143719 | A1* | 6/2005 | Sink ............... A61B 18/203 606/9 |
| 2007/0213693 | A1 | 9/2007 | Plunkett |
| 2008/0247431 | A1 | 10/2008 | Feklistov |
| 2008/0253419 | A1 | 10/2008 | Feklistov |
| 2009/0103200 | A1 | 4/2009 | Feklistov et al. |
| 2010/0049173 | A1 | 2/2010 | Plunkett et al. |
| 2010/0152716 | A1 | 6/2010 | Previn et al. |
| 2011/0098692 | A1 | 4/2011 | Shazly et al. |
| 2013/0110092 | A1 | 5/2013 | Yee |
| 2013/0141672 | A1 | 6/2013 | Smith |
| 2014/0094783 | A1 | 4/2014 | Abe |
| 2014/0180264 | A1 | 6/2014 | Diao et al. |
| 2015/0100049 | A1* | 4/2015 | Mordaunt ........... A61F 9/00823 606/5 |
| 2015/0247199 | A1 | 9/2015 | Fletcher et al. |
| 2017/0000648 | A1* | 1/2017 | Chabrier ............. A61F 9/00821 |
| 2018/0368915 | A1 | 12/2018 | Xia et al. |
| 2019/0282403 | A1 | 9/2019 | Barrett et al. |

FOREIGN PATENT DOCUMENTS

| | | |
|---|---|---|
| JP | 2014-68909 A | 4/2014 |
| WO | WO 2003/049892 A2 | 6/2003 |
| WO | WO 2007/035855 A2 | 3/2007 |
| WO | WO 2015/097150 A2 | 7/2015 |

OTHER PUBLICATIONS

WIPO Application No. PCT/AU2016/051228, PCT International Search Report dated Mar. 9, 2017.
WIPO Application No. PCT/AU2016/051228, PCT Written Opinion of the International Searching Authority dated Mar. 9, 2017.
JP 2018-549370 Office Action dated Nov. 4, 2020, English Translation.

* cited by examiner

PATTERN LASER

CROSS-REFERENCE TO RELATED APPLICATIONS

The present application is the US national stage of PCT/AU2016/051228 filed Dec. 14, 2016 incorporated by reference in its entirety for all purposes, which claims the benefit of AU 2015905168 filed Dec. 14, 2015.

FIELD OF THE INVENTION

The present invention relates to the field of laser devices and in particular to an ophthalmic laser device for treatment of eye problems. The invention also relates to methods of using the ophthalmic laser device.

BACKGROUND TO THE INVENTION

Laser treatment has become well accepted as a preferred modality for many ophthalmic problems. For instance, pan retinal photocoagulation (PRP) using an argon ion laser has been used for treatment of diabetic retinopathy. Diabetic retinopathy is the leading cause of visual impairment in working-age adults worldwide. PRP has provided an effective treatment to decrease the risk of severe vision loss in patients with proliferative diabetic retinopathy for several years. More recently pattern scan lasers have been developed as a more effective alternative to PRP.

A typical pattern scan laser is described in U.S. Pat. No. 7,766,903 titled "Patterned Laser Treatment of the Retina" and issued to The Board of Trustees of the Leland Stanford Junior University. The pattern scan laser generates an output spot that is sequentially moved from location to location on the retina in a selectable pattern. A scanner is used to direct the laser spot. The treatment system operates in the manner of a raster scan according to a particular pattern.

Another example is described in U.S. Pat. No. 8,512,319 titled "Ophthalmic Laser Treatment Apparatus" and issued to Nidek Co. Ltd. The patent describes a system including a separate hand-held cabinet and a main unit that holds a laser unit. A fibre bundle connects the main unit to the hand-held unit. A scanner in the main unit is controlled to direct a laser beam from the laser unit onto the face of the fibre bundle in a selectable manner. The pattern is imaged from the exit of the fibre bundle onto the retina by optics in the hand-held unit.

United States patent publication number 20070121069 titled "Multiple Spot Photomedial Treatment using a Laser Indirect Ophthalmoscope" and filed by Anderson et al describes a beam multiplier that produces a pattern of multiple spots or a scanned pattern. The beam multiplier is described as comprising various combinations of lenses and mirrors to either scan a single input beam to multiple points or split a single input beam into multiple output beams.

U.S. Pat. No. 7,090,670 assigned to Reliant Technologies Inc describes a method of scanning an array of light beams along a main scan direction while dithering in a sub-scan direction. The Reliant Technologies implementation improves scan time by delivering the laser beams through a linear array of optical fibres and mechanically scanning the linear array across the target. This arrangement is faster than some of the prior art but lacks flexibility due to the need for physical adjustment of the direction of the light beams.

Another laser treatment device is described by Reliant Technologies Inc in International Publication number WO 03/049892. This publication describes combining multiple laser beams into a single treatment beam. Each laser beam has at least one distinct parameter. The idea is that specific laser beams can be turned on or off to produce a combined laser beam that has a desirable set of specific parameters. The device does not produce a pattern scan laser.

The known systems identified above have a number of shortcomings. Those devices that are based on beam scanning usually employ galvanic scanning devices that are expensive. There are also significant maintenance costs to maintain the galvanic scanners in reliable working order. Even if other devices are used to reduce cost, such as the mirrors and lenses of US20070121069, the time taken to scan a spot across a pattern on the retina is a significant limitation to the treatments available.

The time required to deliver a pattern is constrained by the time taken to generate that pattern being the product of the number of delivered spots and the sum of the dwell time per spot and the scan time between spots. For a typical pattern scan laser the scan time between spots takes around 1 millisecond and the typical dwell time per spot is around 20 microseconds. Dwell times shorter than 10 milliseconds duration are not preferred as short pulse exposures cause disruptive rather than thermal tissue interactions. This reduces the range of the therapeutic window which means the surgeon loses the ability to predict dosimetry for effective photocoagulation. Exposure durations longer than 30 milliseconds extend the total treatment time beyond practical limits for all but small patterns limited to less than about 10 spots.

An alternate solution is required to extend the usefulness of pattern scan lasers in ophthalmology.

SUMMARY OF THE INVENTION

In one form, although it need not be the only or indeed the broadest form, the invention resides in an ophthalmic pattern laser comprising:

a plurality of laser assemblies each laser assembly including at least a treatment laser device emitting a treatment laser beam;

an optical fibre associated with each laser assembly, the optical fibres being arranged into a fibre bundle;

an optical coupling module associated with each laser assembly and each optical fibre wherein the optical coupling module couples a treatment laser beam into an associated optical fibre;

a controller that controls the operation of the laser devices by selectively turning on or off one or more of the laser devices so as to form a laser treatment pattern of laser spots at an end of the fibre bundle away from the laser devices; and a delivery system that images the output from the fibre bundle to a treatment zone.

In a preferred form of the invention the delivery system simultaneously delivers all the laser spots of the laser treatment pattern in a single exposure. In an alternate form the laser spots of the laser treatment pattern are delivered sequentially.

In another preferred form of the invention each laser assembly further includes an aiming laser as well as a treatment laser. The treatment laser suitably operates in a range from 500 nm to 1100 nm, most suitably in the range 510 nm to 690 nm. The aiming laser is suitably in the visible part of the spectrum, most suitably operating at 635 nm. The optical coupling module couples an aiming laser beam and a treatment laser beam into each optical fibre.

The optical fibres are suitably gathered into a close packed fibre bundle at a delivery end and separated at an input end.

The controller suitably also controls other laser parameters including power, pulse duration, time between pulses, zoom, pattern selection and pattern mode (sequential or simultaneous).

In a further form the invention resides in an ophthalmic pattern laser comprising:
a plurality of laser assemblies each laser assembly including at least a treatment laser device emitting a treatment laser beam and an aiming laser device emitting an aiming laser beam;
an optical fibre associated with each laser assembly, the optical fibres being arranged into a fibre bundle;
an optical coupling module associated with each laser assembly and each optical fibre wherein the optical coupling module couples a treatment laser beam and an aiming laser bean into an associated optical fibre;
a controller that controls the operation of the laser devices by selectively turning on or off one or more of the laser devices so as to form a laser aiming pattern or a laser treatment pattern of laser spots at an end of the fibre bundle away from the laser devices; and
a delivery system that images the output pattern from the fibre bundle to a treatment zone to simultaneously deliver all the laser spots of the selected laser treatment pattern in a single exposure.

In another form the invention resides in a method of applying a laser pattern to a treatment zone including the steps of:
forming an optical fibre bundle having a close packed and patterned arrangement at one end and separated fibres at an opposite end;
associating a laser assembly with each optical fibre of the optical fibre bundle through an optical coupler, each laser assembly including at least a treatment laser device such that laser radiation emitted from the treatment laser device is coupled into an optical fibre;
controlling the operation of the treatment laser devices by selectively turning on or off one or more of the treatment laser devices so as to form a laser treatment pattern at an end of the fibre bundle away from the laser devices; and
delivering the laser treatment pattern to a treatment zone by imaging the pattern of the fibre bundle.

The method may further include the step of selecting the treatment zone using an aiming laser included in the laser assembly.

Further features and advantages of the present invention will become apparent from the following detailed description.

BRIEF DESCRIPTION OF THE DRAWINGS

To assist in understanding the invention and to enable a person skilled in the art to put the invention into practical effect, preferred embodiments of the invention will be described by way of example only with reference to the accompanying drawings, in which.

DETAILED DESCRIPTION OF THE INVENTION

Figure 1:
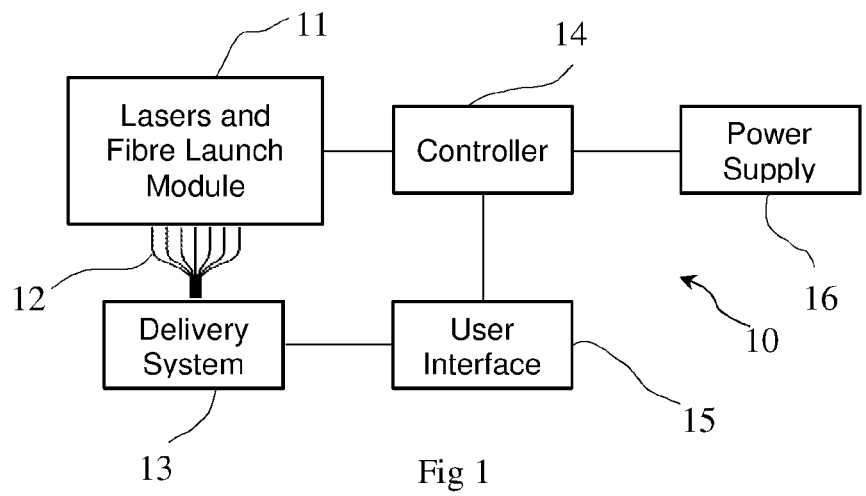
FIG. 1 is a block diagram of a pattern laser.

Embodiments of the present invention reside primarily in a pattern laser and method of using a pattern laser. Accordingly, the elements of the pattern laser have been illustrated in concise schematic form in the drawings, showing only those specific details that are necessary for understanding the embodiments of the present invention, but so as not to obscure the disclosure with excessive detail that will be readily apparent to those of ordinary skill in the art having the benefit of the present description.

In this specification, adjectives such as first and second, left and right, and the like may be used solely to distinguish one element or action from another element or action without necessarily requiring or implying any actual such relationship or order. Words such as "comprises" or "includes" are intended to define a non-exclusive inclusion, such that a process, method, article, or apparatus that comprises a list of elements does not include only those elements but may include other elements not expressly listed, including elements that are inherent to such a process, method, article, or apparatus.

Referring to FIG. 1 there is a shown a block diagram of a pattern laser 10 useful for pan retinal photocoagulation (PRP) and other applications. The pattern laser 10 comprises a laser and fibre launch module 11, described in more detail below. Optical fibres from the laser and fibre launch module 11 are formed into a close packed bundle 12 which is coupled to a delivery system 13 that images the output from the bundle 12 to a treatment zone. The operation of the lasers in the laser and fibre launch module 11 is controlled by a controller 14. A user interface 15 allows user input to the controller 14 to control the operation of the lasers to, inter alia, form patterns. The user interface 15 may also permit control of the delivery system 13. Power for the pattern laser 10 is provided by power supply 16.

Figure 2:
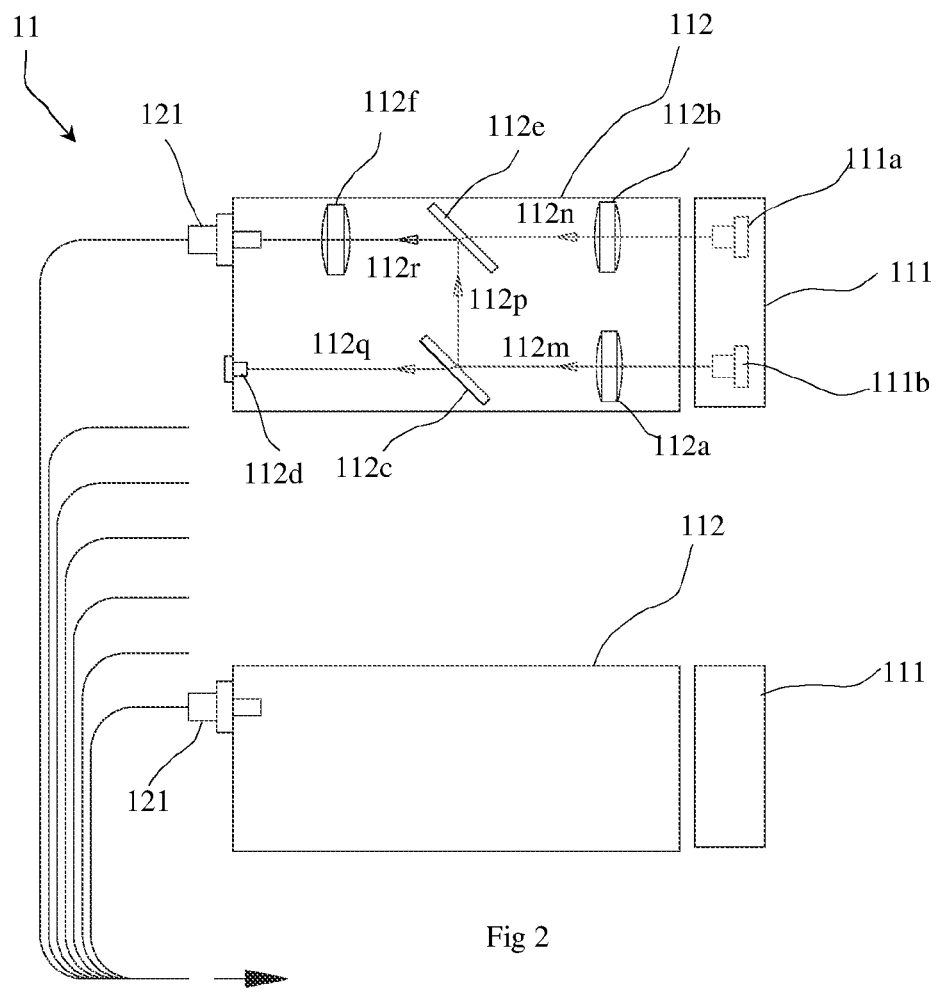
FIG. 2 is a schematic of a coupling module of the pattern laser of FIG. 1.

Referring to FIG. 2, the laser and fibre launch module 11 is shown in greater detail. For ease of explanation the pattern laser 10 is described as comprising seven pair of treatment and aiming lasers and seven associated optical fibres that are formed into a close packed bundle at the output end, spaced regularly (for example, being a filled hexagon). It will be appreciated that there is effectively no limit to the number of fibres and lasers other than cost. The module 11 includes seven pair of diode laser assemblies 111, each containing an aiming diode 111a and a treatment diode 111b, which are conveniently packed into a practical arrangement. There is a corresponding optical fibre 121 associated with each pair of laser diode assemblies 111. An optical coupler 112 couples the output from the laser diode assemblies 111 into the optical fibre 121. The optical coupler 112 comprises collimating lenses, 112a and 112b, for the divergent laser beams emitted from aiming diode 111a and treatment diode 111b respectively. The collimated treatment beam 112m is split by a beam splitter 112c into two paths. The majority is reflected towards the aiming laser path 112p. A small amount 112q is transmitted and projected onto a power detector 112d which monitors the power output of the treatment diode 111b. The reflected treatment beam 112p is combined with the aiming beam 112n by the beam combiner 112e into the same optical path 112r. The combined beams are focused onto the fibre 121 at the input end by the focusing lens 112f in such a way that the aiming laser and the treatment laser are always on the same optical path so that the aiming laser helps the user to target the treatment site. The optical coupler 112 may be locked once set so that further adjustment should not be required.

Suitable treatment laser diodes 111b operate in (but are not limited to) the green portion of the visible spectrum for many ophthalmic applications. A suitable laser diode operates in a wavelength range of 510-690 nm. The invention is not limited to this particular laser diode, or to the particular wavelength range. Laser diodes operating at any wavelength in the available spectrum may be suitable for certain applications. The inventors have found that the laser diodes are most suitable because of the compact lightweight design, low cost, and easy availability at a number of different operating wavelengths. However, the laser source is not limited to diode lasers. A red laser operating at 635 nm is a good option for the aiming laser 111a.

Figure 3:
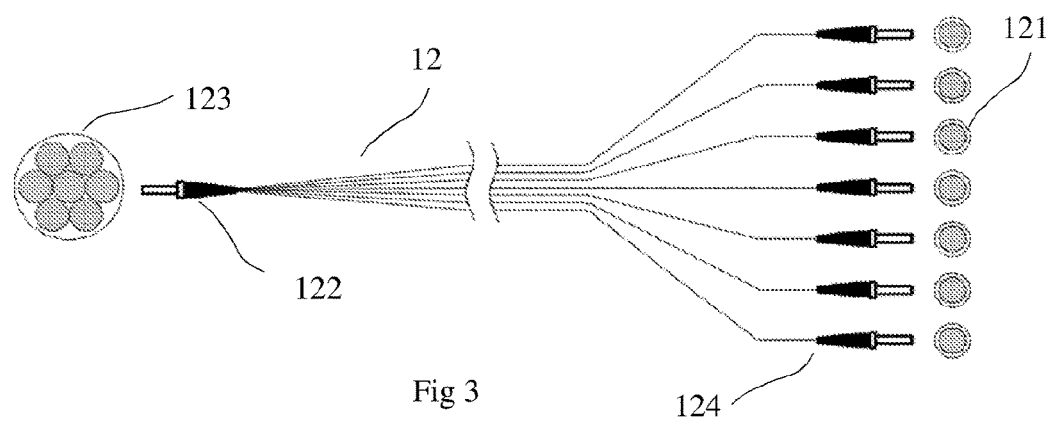
FIG. 3 is a schematic of a fibre bundle of the pattern laser of FIG. 1.

The optical fibres 121 are formed into a fibre bundle 12 as shown in FIG. 3. The bundle 12 in the embodiment shown has seven fibres but the inventors consider that anywhere from 3 to 19 fibres, could form the bundle, although even more is possible. The fibre bundle is preferably arranged in a regularly spaced array, including but not limited to a filled hexagonal shape. The fibres may be single-mode or multi-mode. Suitable fibres are multi-mode fibre with a core diameter range from 10 μm to 200 μm. The bundle 12 may be held together at a distal end 122 by adhesive or other bonding methods to form a close packed tip 123. The close packed tip 123 is suitably potted in a fibre connector, such as SMA, ST, FC, etc. The preferred packing is hexagonal so the preferred number of fibres in the bundle is 7 or 19. The bundle splits into single fibres 121 at a near end 124 and each fibre terminates in a suitable fibre connector to mate with the optical coupler 112 described above.

Figure 4:
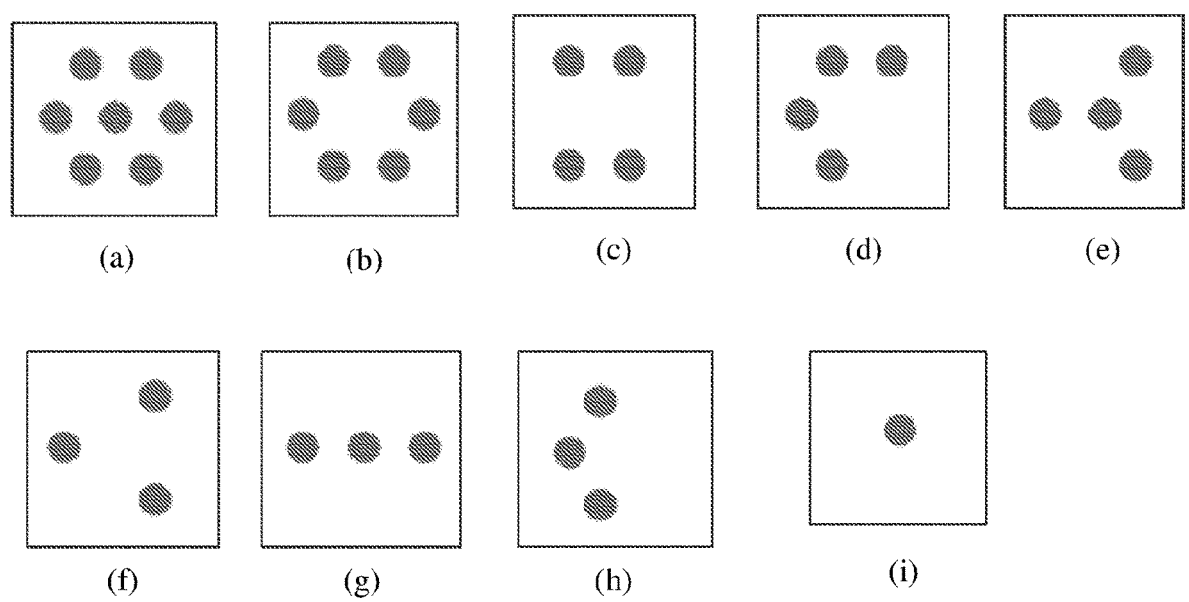
FIG. 4 shows examples of various treatment patterns.

Various output patterns may be produced by controlling the operation of the laser diode assemblies 111. The controller 14 may turn on or off each laser diode individually. Thus a spot pattern may be formed simultaneously by turning all selected laser devices off and on at the same time, or sequentially by turning selected laser devices on and off in sequence. The controller may also vary the power output of each laser diode as well as other parameters such as how long each laser diode remains on and off. Various possible patterns for the preferred embodiment are shown in FIG. 4. As can be seen in FIG. 4(a), the output will be from all seven optical fibres when all laser diodes are switched on. The central fibre will be dark as shown in FIG. 4(b) if the appropriate single laser diode is not switched on by the controller. If four laser diodes are switched on the pattern of FIG. 4(c), FIG. 4(d) or FIG. 4(e) are formed. Only switching on three laser diodes can produce the pattern of FIG. 4(f), FIG. 4(g) or FIG. 4(h) and only switching on one laser diode can produce a single spot as shown in FIG. 4(i). The patterns depicted in FIG. 4 are only a selection of available patterns that may be produced.

The laser diodes of a selected pattern can be controlled to turn on simultaneously or sequentially. In the setting of sequential mode the patterned laser will be scanned on the targeted treatment area.

The patterns may be produced automatically by the controller 14 upon selection of a treatment modality or maybe selected manually by the user through the User Interface 15.

The User Interface 15 may suitably be a touch screen that allows a user to select between a range of preset applications. It may also include a manual mode that displays a representation of the fibre bundle tip 123 that allows a user to touch an individual fibre to activate output. The User Interface also allows management of the other factors such as pulse duration, time between pulses, power level, selection of pattern, pattern delivery mode, etc.

One significant advantage of this invention is all the pattern spots can be delivered simultaneously as a single array at a clinically optimal pulse duration being in the 1 millisecond to 1000 millisecond range. Most clinicians have a good understanding of coagulation dynamics in this exposure range where the therapeutic window is optimum. With this invention the optimum performance can be achieved easily and the consequence of turning on all the laser sources simultaneously eliminates the constraint of the dwell time of each individual spot in the pattern. Using a conventional pattern scan laser to deliver a 10-spot pattern with an optimal 50 ms dwell time of each spot takes more than 500 ms for each pattern delivery. If a 10-spot pattern of this invention is used with a 50 ms dwell time, it only takes 50 ms for the pattern delivery in the simultaneous mode.

The further consequence of this is that the array can be moved as a block to a fresh area and a subsequent exposure can be delivered sequentially hence a large area can be covered very quickly by repeating this process.

It will be appreciated that the ophthalmic patter laser described above does not utilize any form of scanning or dithering to produce the treatment pattern. The treatment pattern is determined by turning on or off individual treatment lasers which are coupled to individual fibres in the optical fibre bundle.

Figure 5:
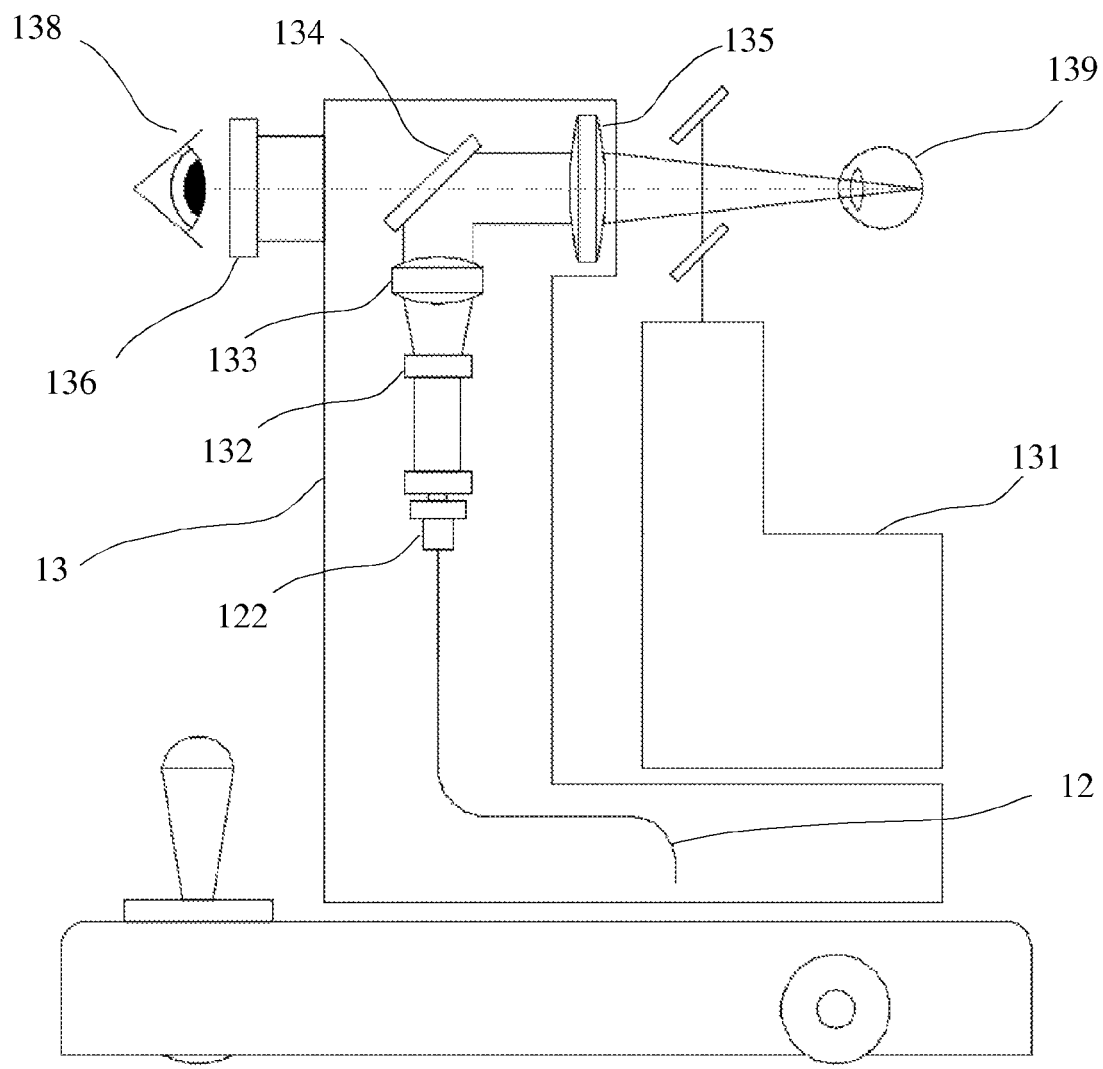
FIG. 5 shows a slit lamp assembly for use with the invention.

Referring to FIG. 5, the fibre bundle 12 is coupled to a delivery system 13, such as a slit lamp assembly. The slit lamp delivery system consists of a slit lamp illuminator 131, a zooming module 132, a beam collimator 133, a mirror 134, and a focusing lens 135. The ophthalmologist 138 can observe the back of the patient's eye 139 through the eyepiece 136 of the slit lamp microscope and the delivery of the laser pattern to a treatment zone on the retina as the laser beam is redirected by the mirror 134 to the viewing path. The distal end 122 of the fibre bundle 12 is connected to the zoom module 132 by which the spot size and spacing of the patterns can be scaled up as desired. A user is able to manipulate the distal end 122 of the fibre bundle 12 to accurately position the output of the fibre bundle as desired. Most clinicians are familiar with the slit lamp so it enhances the usability of the pattern laser. Other delivery systems will be appropriate in other applications, such as a slitlamp adaptor which can be mounted on the slitlamp microscope which is popularly used by ophthalmologists, or laser indirect ophthalmoscope (LIO).

Figure 6:
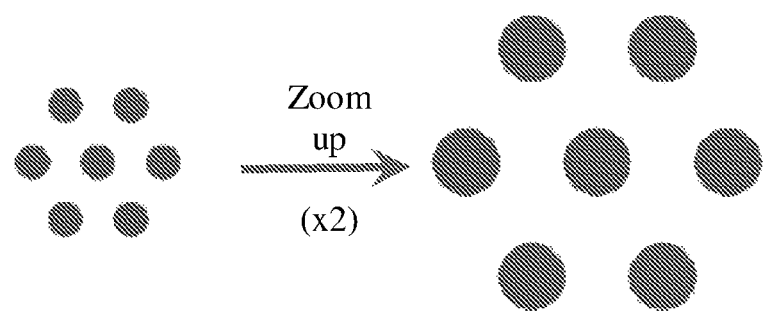
FIG. 6 exemplifies zooming.

As well as changing the laser spot pattern as described above with reference to FIG. 4, the user can also scale the size of the spot pattern by adjusting the zoom module 132. The effect of zoom adjustment is shown in FIG. 6. The pattern size may be scaled by fixed steps, such as 2×, 4×, 6×, 10×, 20× etc or may be continuously adjustable. It will be noted that both the spot size and the pattern size are scaled.

The above description of various embodiments of the present invention is provided for purposes of description to one of ordinary skill in the related art. It is not intended to be exhaustive or to limit the invention to a single disclosed embodiment. As mentioned above, numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. Accordingly, this invention is intended to embrace all alternatives, modifications and variations of the present inven-

The invention claimed is:

1. An ophthalmic pattern laser for treatment of an eye problem comprising:
   a plurality of laser assemblies each laser assembly including at least a treatment laser device emitting a treatment laser beam and an aiming laser device emitting an aiming laser beam;
   an optical fibre associated with each laser assembly, the optical fibres being arranged into a fibre bundle;
   an optical coupling module associated with each laser assembly and each optical fibre wherein the optical coupling module couples a treatment laser beam and an aiming laser beam into the associated optical fibre;
   a controller that controls the operation of the laser devices without any form of scanning or dithering to produce a treatment aiming pattern or a laser treatment pattern by selectively turning on or off one or more of the laser devices so as to form the laser aiming pattern or the laser treatment pattern of laser spots at an end of the fibre bundle away from the laser devices; and
   a delivery system that directs the output from the fibre bundle to a treatment zone wherein the fibre bundle remains stationary during the treatment.

2. The ophthalmic pattern laser of claim 1 wherein the delivery system simultaneously delivers all the laser spots of the laser treatment pattern in a single exposure.

3. The ophthalmic pattern laser of claim 1 wherein the delivery system sequentially delivers all the laser spots of the laser treatment pattern.

4. The ophthalmic pattern laser of claim 1 wherein the treatment laser device emits a treatment laser beam with a wavelength in a range from 500 nm to 1100 nm.

5. The ophthalmic pattern laser of claim 1 wherein the treatment laser device emits a treatment laser beam with a wavelength in a range from 510 nm to 690 nm.

6. The ophthalmic pattern laser of claim 1 wherein the aiming laser device emits the aiming laser beam with a wavelength in the visible spectrum.

7. The ophthalmic pattern laser of claim 1 wherein the aiming laser device emits the aiming laser beam with a wavelength of 635 nm.

8. The ophthalmic pattern laser of claim 1 wherein the optical coupling module comprises collimating lenses, a beam combiner and focusing lenses to combine the aiming laser beam and treatment laser beam and direct the combined beam to the optical fibre.

9. The ophthalmic pattern laser of claim 1 wherein the optical fibres are gathered into a close packed fibre bundle at a delivery end and separated into a spaced array at an input end.

10. The ophthalmic pattern laser of claim 1 comprising seven treatment laser devices and seven optical fibres wherein the seven optical fibres are bundled in a hexagon shape at the end of the fibre bundle away from the laser devices.

11. The ophthalmic pattern laser of claim 1 wherein the controller also controls other laser parameters including one or more of: power; pulse duration; dwell time; zoom; pattern selection; and pattern mode.

12. The ophthalmic pattern laser of claim 1 wherein the laser devices are laser diodes.

13. The ophthalmic pattern laser of claim 1 further comprising a user interface that allows a user to input to the controller.

14. The ophthalmic pattern laser of claim 1, wherein the optical fibres being arranged into the fibre bundle are arranged in a regularly spaced array having a first shape, wherein the laser aiming pattern or the laser treatment pattern is bounded by the first shape.

15. The ophthalmic pattern laser of claim 14, wherein the first shape is a two-dimensional shape, wherein the laser aiming pattern or the laser treatment pattern corresponds to the two-dimensional shape.

16. A method of applying a laser pattern to a treatment zone of an eye problem including the steps of:
   forming an optical fibre bundle having a close packed arrangement at one end and a spaced array at an opposite end;
   associating a laser assembly with each optical fibre of the optical fibre bundle through an optical coupler, each laser assembly including at least a treatment laser device emitting a treatment laser beam and an aiming laser device emitting an aiming laser beam such that the treatment laser beam and the aiming laser beam are coupled into an optical fibre;
   controlling the operation of the treatment laser devices and aiming laser devices by selectively turning on or off one or more of the treatment laser devices and/or aiming laser devices so as to form a laser treatment pattern at an end of the fibre bundle away from the laser devices without any form of scanning or dithering to produce the treatment pattern; and
   delivering the laser treatment pattern to a treatment zone while the fibre bundle remains stationary.

17. The method of claim 16 further including the step of selecting the treatment zone using the aiming laser beam.

18. The method of claim 16, wherein the spaced array at the opposite end of the optical fibre bundle comprises a spaced array having a two-dimensional shape, wherein the treatment pattern corresponds to the two-dimensional shape.

* * * * *